US009566055B2

(12) United States Patent
Sasaki et al.

(10) Patent No.: US 9,566,055 B2
(45) Date of Patent: Feb. 14, 2017

(54) CANNULA WITH DEPLOYABLE ANCHOR WIRE AND METHODS OF USE

(71) Applicant: Kyphon SARL, Neuchatel (CH)

(72) Inventors: Neil Sasaki, San Jose, CA (US); Craig Lauchner, Mountain View, CA (US)

(73) Assignee: Kyphon SÀRL, Neuchâtel (CH)

( * ) Notice: Subject to any disclaimer, the term of this patent is extended or adjusted under 35 U.S.C. 154(b) by 367 days.

(21) Appl. No.: 14/311,622

(22) Filed: Jun. 23, 2014

(65) Prior Publication Data

US 2015/0366552 A1 Dec. 24, 2015

(51) Int. Cl.
*A61B 17/02* (2006.01)
*A61B 1/32* (2006.01)
*A61B 17/34* (2006.01)

(52) U.S. Cl.
CPC ............. *A61B 17/0218* (2013.01); *A61B 1/32* (2013.01); *A61B 17/02* (2013.01); *A61B 17/0293* (2013.01); *A61B 17/34* (2013.01); *A61B 2090/309* (2016.02); *A61B 2090/3966* (2016.02)

(58) Field of Classification Search
CPC ....... A61B 1/32; A61B 17/02; A61B 17/0218; A61B 17/0293; A61B 17/34; A61B 17/3417; A61B 17/3421; A61B 17/3439; A61B 2017/348; A61B 2017/3482; A61B 2017/3484
See application file for complete search history.

(56) References Cited

U.S. PATENT DOCUMENTS

| 5,333,624 | A | 8/1994 | Tovey |
| 5,364,408 | A | 11/1994 | Gordon |
| 5,397,331 | A | 3/1995 | Himpens et al. |
| 5,486,197 | A | 1/1996 | Le et al. |
| 5,527,343 | A | 6/1996 | Bonutti |
| 5,941,900 | A | 8/1999 | Bonutti |
| 6,652,563 | B2 | 11/2003 | Dreyfuss |
| 7,833,238 | B2 | 11/2010 | Nakao |
| 8,551,139 | B2 | 10/2013 | Surti et al. |
| 2005/0267479 | A1 | 12/2005 | Morgan et al. |
| 2010/0240961 | A1* | 9/2010 | Aferzon .................... A61B 1/32 600/212 |

* cited by examiner

*Primary Examiner* — Larry E Waggle, Jr.

(57) ABSTRACT

A surgical instrument includes a first member comprising an end surface. A second member includes a flange and a first groove having a holding member movably disposed therein. A third member includes a lip and a second groove having the holding member movably disposed therein. The lip extends at an acute angle relative to an axis defined by the third member. The holding member is movable between a first configuration in which the holding member is disposed in the second groove and first and second portions of the holding member are positioned in the first groove and a second configuration in which the holding member is spaced apart from the second groove and the first and second portions of the holding member are spaced apart from the first groove. Systems and methods are disclosed.

20 Claims, 7 Drawing Sheets

CANNULA WITH DEPLOYABLE ANCHOR WIRE AND METHODS OF USE

TECHNICAL FIELD

The present disclosure generally relates to medical devices for the treatment of musculoskeletal disorders, and more particularly to a surgical system and method for accessing a surgical site to facilitate treatment.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. Surgical retractors may be employed during a surgical treatment to provide access and visualization of a surgical site. Such retractors space apart and support tissue and/or other anatomical structures to expose anatomical structures adjacent the surgical site and/or provide a surgical pathway to the surgical site. This disclosure describes an improvement over these prior art technologies.

SUMMARY

In one embodiment, a surgical instrument is provided. The surgical instrument comprises a first member comprising an end surface and a body including an inner surface defining a throughhole. A second member extends along a first longitudinal axis between a first end comprising a flange and an opposite second end comprising a first groove having a holding member movably disposed therein. The second member comprises an inner surface defining a passageway. A third member extends along a second longitudinal axis between a first end comprising a lip and an opposite second end that is movably positioned in the passageway. The lip extends at an acute angle relative to the second longitudinal axis. The second end of the third member comprises a second groove having the holding member movably disposed therein. The holding member is movable between a first configuration in which the holding member is disposed in the second groove and first and second portions of the holding member are positioned in the first groove and a second configuration in which the holding member is spaced apart from the second groove and the first and second portions of the holding member are spaced apart from the first groove. In some embodiments, systems and methods are provided.

BRIEF DESCRIPTION OF THE DRAWINGS

The present disclosure will become more readily apparent from the specific description accompanied by the following drawings, in which.

DETAILED DESCRIPTION

The exemplary embodiments of a surgical system and related methods of use disclosed are discussed in terms of medical devices for the treatment of musculoskeletal disorders and more particularly, in terms of a surgical system and method for accessing a surgical site to facilitate treatment. In one embodiment, the surgical system includes a surgical instrument, such as, for example, a cannula that reduces costs and provides unique features that address unmet needs. In some embodiments, the surgical instrument includes one or a plurality of light sources, such as, for example, light emitting diodes (LEDs) at a distal end of the surgical instrument for illuminating a patient's anatomy, thereby increasing effective visualization. In some embodiments, the surgical instrument includes one or a plurality of light sources, such as, for example, light emitting diodes (LEDs) at a proximal end of the surgical instrument for illuminating a patient's anatomy, thereby increasing effective visualization. In some embodiments, the surgical instrument includes light pipes for increasing effective visualization. In some embodiments, the surgical instrument is configured for use by medical practitioners, such as, for example, interventionalists in connection with surgical procedures, such as, for example, decompression procedures. In some embodiments, the surgical instrument is configured for use in decompression procedures in which the patient remains conscious. During such procedures, surgical instruments are typically pushed dorsally as the patient's dorsal muscles contract, such as, for example, when the patient lifts his or her head. Accordingly, the disclosed surgical instrument is configured to remain stationary as a patient moves, thus avoiding unintended movement of the surgical instrument. In some embodiments, the surgical instrument creates an anchor by deploying a wire as the instrument moves from an unexpanded configuration to an expanded configuration such that the wire engages tissue to prevent movement of the instrument. In some embodiments, the wire comprises nitinol or spring steel configured to push into surrounding muscle while the instrument expands, effectively holding the instrument in place in the event of patient movement. Holding the instrument in place prevents the need to reposition the instrument in response to patient movement as well as the need to control fresh bleeding.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and methods of employing the surgical system in accordance with the principles of the present disclosure. Alternate embodiments are also disclosed. Reference will now be made in detail to the exemplary embodiments of the present disclosure, which are illustrated in the accompanying figures. Turning to FIGS. 1-18, there are illustrated components of a surgical system 20 including a surgical instrument, such as, for example, a cannula or retractor 22, in accordance with the principles of the present disclosure.

The components of surgical system 20 can be fabricated from biologically acceptable materials suitable for medical applications, including metals, synthetic polymers, ceramics and bone material and/or their composites, depending on the particular application and/or preference of a medical practitioner. For example, the components of surgical system 20, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as potyaetide, polyglycolide, polytyrosine carbonate, polycaroplaetohe and their combinations. Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Cannula 22 includes a first member 24, such as, for example, a top nut comprising a body 26 including an inner surface 28 defining a throughhole 30 having a cylindrical cross sectional configuration. In some embodiments, surface 28 comprises an internal thread form 32, best shown in FIGS. 1A, 2A and 2O, configured to engage an external thread form 34 on an outer surface 36 of an end 38 a second member 40, as will be described. In some embodiments, throughhole 30 may have various cross section configurations, such as, for example, oval, oblong, triangular, rectangular, square, polygonal, irregular, uniform, non-uniform, variable, tubular and/or tapered. In some embodiments, member 24 can be variously connected with member 40, such as, for example, monolithic, integral connection, frictional engagement, threaded engagement, mutual grooves, screws, adhesive, nails, barbs and/or raised element. In some embodiments, an outer surface 42 of member 24 opposite surface 28 includes a plurality of spaced apart projections defining notches 46 therebetween configured for gripping by a medical practitioner. In some embodiments, notches 46 are concavely curved between adjacent projections. In some embodiments, surface 42 may have various surface configurations to enhance gripping thereof, such as, for example, rough, arcuate, undulating, porous, semi-porous, dimpled, polished and/or textured. In some embodiments, all or only a portion of notches 46 may be variously configured and dimensioned, such as, for example, planar, concave, polygonal, irregular, uniform, non-uniform, staggered, tapered, consistent or variable.

Figure 1:
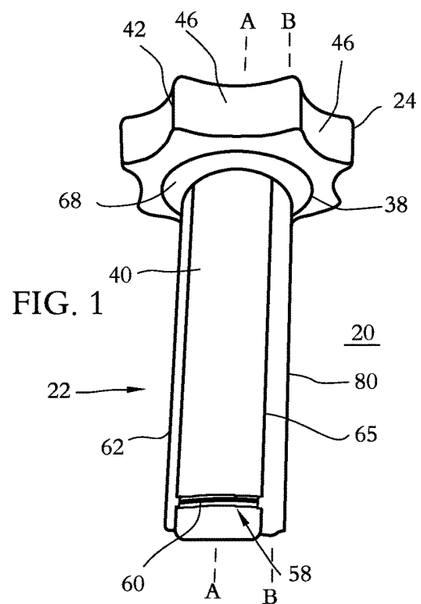
FIG. 1 is a perspective view of components of one embodiment of a surgical system in accordance with the principles of the present disclosure.
Figure 1A:
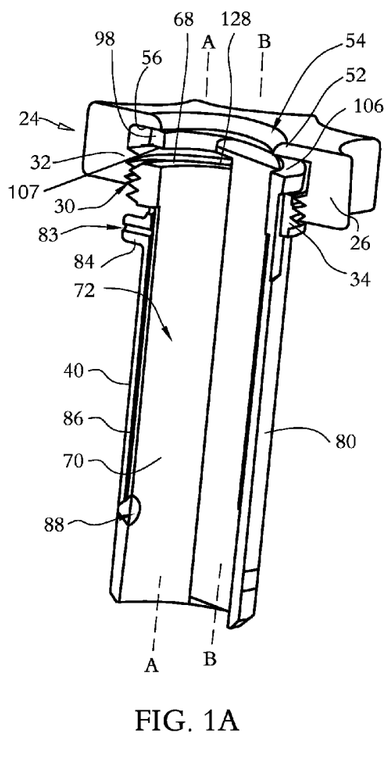
FIG. 1A is a perspective, cross sectional view of components shown in FIG. 1.
Figure 2:
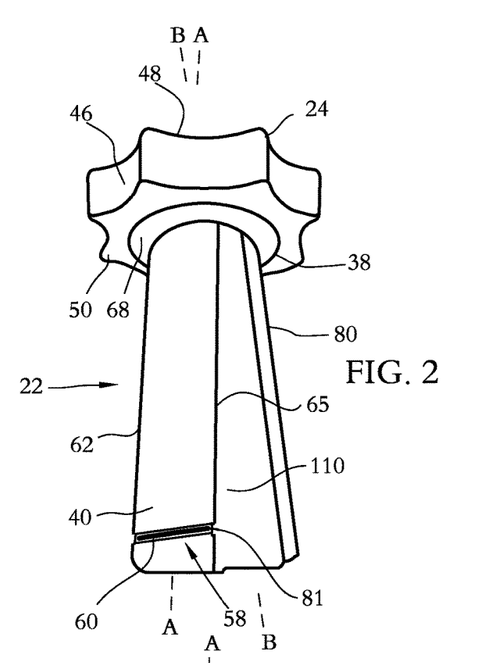
FIG. 2 is a perspective view of components shown in FIG. 1.
Figure 2A:
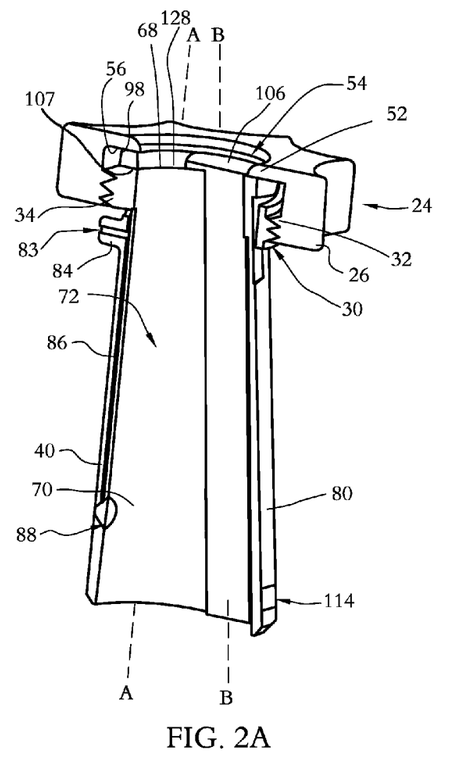
FIG. 2A is a perspective, cross sectional view of components shown in FIG. 1.
Figure 3:
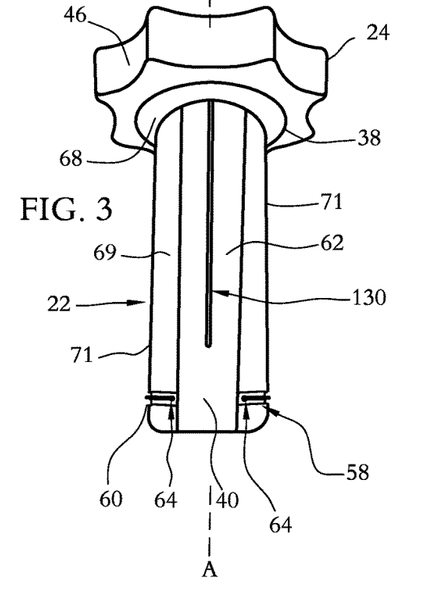
FIG. 3 is a perspective view of components shown in FIG. 1.
Figure 4:
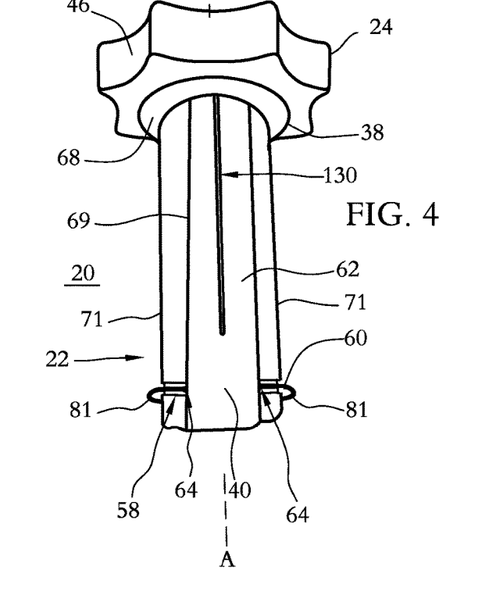
FIG. 4 is a perspective view of components shown in FIG. 1.
Figure 5:
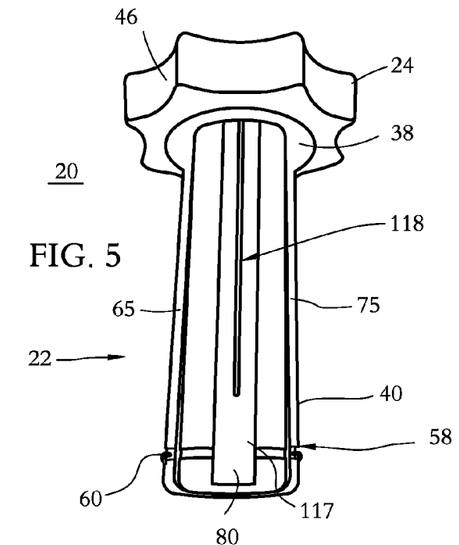
FIG. 5 is a perspective view of components shown in FIG. 1.
Figure 6:
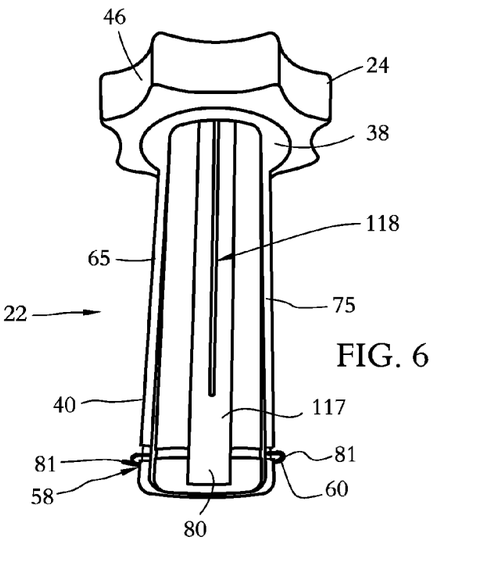
FIG. 6 is a perspective view of components shown in FIG. 1.

Body 26 extends between an end 48 and an opposite end 50. End 48 includes a projection 52 extending inwardly from body 26 toward throughhole 30 and/or a longitudinal axis defined by body 26, as best shown in FIGS. 1A, 2A and 2O. Projection 52 defines a throughhole 54 having a cylindrical cross sectional configuration and a diameter that is less than that of throughhole 30. Projection 52 comprises a planar end surface 56 extending perpendicular to the longitudinal axis defined by body 26. In some embodiments, throughhole 54 may have various cross section configurations, such as, for example, oval, oblong, triangular, rectangular, square, polygonal, irregular, uniform, non-uniform, variable, tubular and/or tapered. In some embodiments, all or only a portion of surface 56 may be variously configured and dimensioned, such as, for example, planar, concave, polygonal, irregular, uniform, non-uniform, staggered, tapered, consistent or variable. In some embodiments, surface 56 may be disposed at alternate orientations, relative to the longitudinal axis defined by body 26, such as, for example, transverse, perpendicular and/or other angular orientations such as acute or obtuse, co-axial and/or may be offset or staggered. In some embodiments, may have various surface configurations to enhance engagement with a lip 98 of a third member 80, such as, for example, rough, arcuate, undulating, porous, semi-porous, dimpled, polished and/or textured, as will be described. In some embodiments, member 24 is made entirely of molded plastic.

Figure 12:
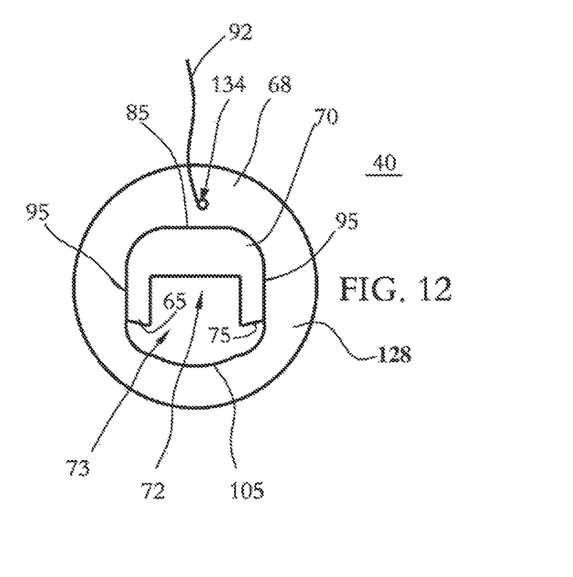
FIG. 12 is a top view of a component shown in FIG. 1.

Member 40 extends along a longitudinal axis A between end 38 and an opposite end 66. End 38 comprises a flange 68 extending perpendicular to axis A. An outer surface of flange 68 has a circular cross sectional configuration in a direction perpendicular to axis A. Member 40 includes an end wall 69 extending between opposite side walls 71. Member 40 comprises an opening 73 opposite wall 69. An inner surface 70 of member 40 is concavely curved at interfaces between side walls 71 and wall 69 such that surface 70 defines a passageway 72 having a U-shaped cross sectional configuration in a direction perpendicular to axis A. Flange 68 defines an opening 74 extending through flange 68. Opening 74 is in communication with passageway 72. In some embodiments, flange 68 includes planar or linear portion 85 extending between planar or linear portions 95 of flange 68, as best shown in FIG. 12. Interfaces between portions 85, 95 are concavely curved. The interfaces between portions 85, 95 are aligned with the interfaces between the inner surfaces of side walls 71 and wall 69 along axis A. Portions 95 extends parallel to one another and, together with inner surfaces of side walls 71, are configured to engage outer surfaces or planar side walls 110 of member 80, as will be discussed. In some embodiments, flange 68 includes an arcuate portion 105 opposite portion 85. Portion 105 is concave. In some embodiments, portion 105 is continuously curved between portions 95. In some embodiments, only a midsection of portion 105 is concave. In some embodiments, passageway 72 and/or opening 74 may have various cross section configurations, such as, for example, oval, oblong, triangular, rectangular, square, polygonal, irregular, uniform, non-uniform, variable, tubular and/or tapered. In some embodiments, flange 68 may be disposed at alternate orientations, relative to axis A, such as, for example, transverse, perpendicular and/or other angular orientations such as acute or obtuse, co-axial and/or may be offset or staggered.

Figures 7, 8:
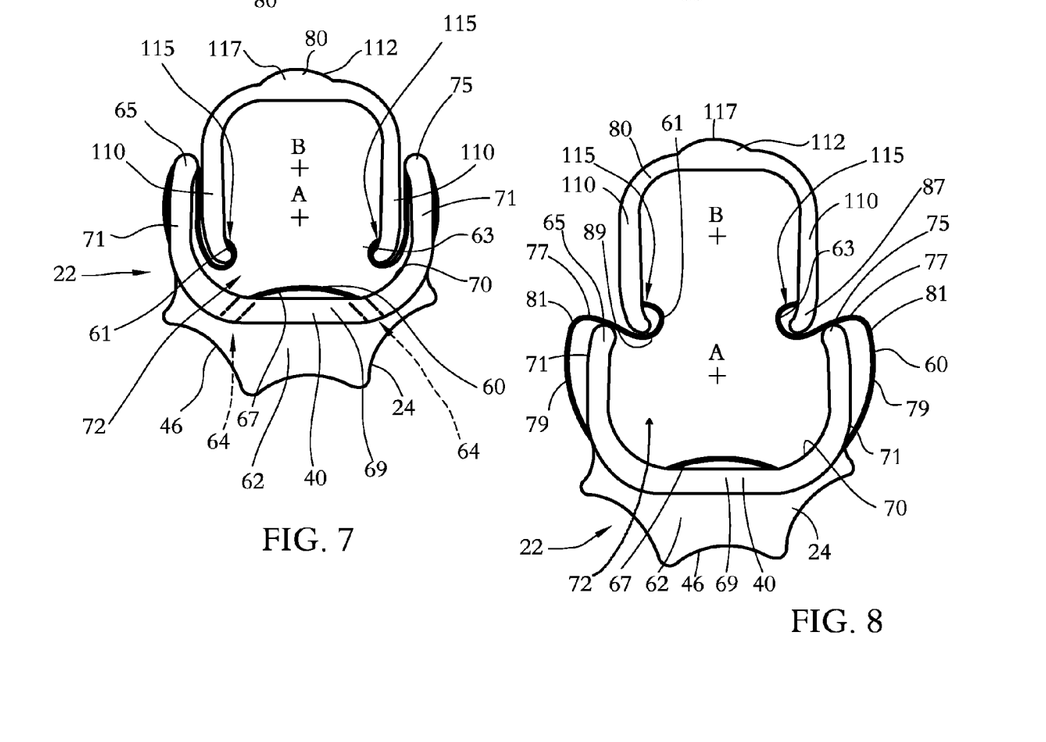
FIG. 7 is a bottom view of components shown in FIG. 1.
FIG. 8 is a bottom view of components shown in FIG. 1.

Member 40 includes a groove 58 extending into an outer surface of member 40 adjacent end 66 configured for movable disposal of a holding member, such as, for example, an anchor wire 60, as will be discussed. In some embodiments, groove 58 extends perpendicular to axis A. In some embodiments, groove 58 extends continuously about the outer surface of member 40. In some embodiments, member 40 comprises a ridge 62 extending outwardly from the outer surface of member 40 that interrupts groove 58. In some embodiments, ridge 62 bisects groove 58 into two equal length portions. That is, groove 58 comprises a first portion on one side of ridge 62 and a second portion on another side of ridge 62. Member 40 comprises openings 64 on either side of ridge 62 configured for disposal of wire 60. One opening 64 is in communication with the first portion of ridge 62 and the other opening 64 is in communication with the second portion of ridge 62. Openings 64 each extend through surface 70 and the outer surface of member 40. Openings 64 each extend transverse to axis A. Ridge 62 extends parallel to axis A. In some embodiments, all or only a portion of groove 58 may be variously configured and dimensioned, such as, for example, planar, concave, polygonal, irregular, uniform, non-uniform, staggered, tapered, consistent or variable. In some embodiments, openings 64 each extend at an acute angle relative to axis A to minimize the amount wire 60 bends between openings 64, as shown in FIGS. 7 and 8. In some embodiments, wire 60 comprises a shape memory material. In some embodiments, wire 60 comprises nitinol. In some embodiments, wire 60 comprises spring steel. In some embodiments, wire 60 comprise perforated spring steel. In some embodiments, member 40 is made entirely of molded plastic.

Figure 13:
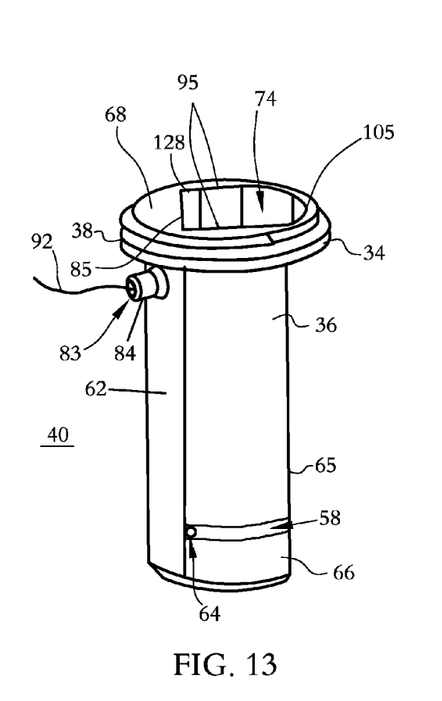
FIG. 13 is a perspective view of a component shown in FIG. 1.
Figure 14:
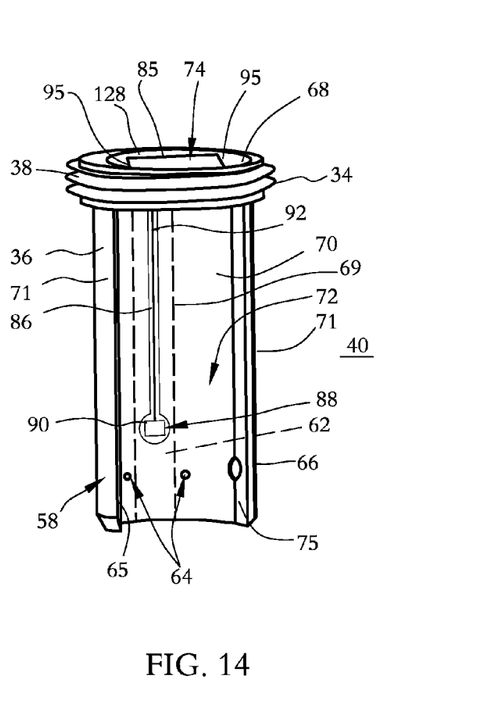
FIG. 14 is a perspective view of a component shown in FIG. 1.

In some embodiments, member 40 comprises a port 84 extending through ridge 62, as shown in FIGS. 1A, 2A and 13. Port 84 includes an opening 83 that is in communication with a lumen 86 defined by surface 70, as shown in FIGS. 1A. 2A and 14. Lumen 86 terminates in a cavity 88 that extends into surface 70 without extending through the outer surface of member 40, as shown in FIG. 14. Lumen 86 also extends into surface 70 without extending through the outer surface of member 40, as also shown in FIG. 14. In some embodiments, lumen 86 does not extend through surface 70 or the outer surface of member 40 such that lumen 86 is embedded within a wall thickness of member 40, and is thus concealed from view. A light source 90, such as, for example, a light emitting diode (LED) is positioned in cavity 88 such that a wire 92 connected to light source 90 extends through lumen 86 and opening 83. In some embodiments, wire 92 is used to provide power to light source 90. Light source 90 is configured to illuminate at least a portion of passageway 72. In some embodiments, light source 90 is embedded within member 40 such that light source 90 is permanently fixed to member 40. In some embodiments, light source 90 is embedded within member 40 and at least a portion of member 40 is transparent or translucent to allow light from light source 90 to pass through member 40. In some embodiments, cannula 22 includes a battery configured to power light source 90. In some embodiments, light source 90 does not extend through port 84 or lumen 86 and is adhered or otherwise attached to surface 70. In some embodiments, member 40 includes one or a plurality of light sources 90. In some embodiments, light sources 90 are variously positioned along member 40. In some embodiments, member 40 comprises at least one light source 90 at end 38. In some embodiments, member 40 comprises at least one light source 90 at end 66. In some embodiments, member 40 comprises at least one light source 90 positioned between ends 38, 66.

Figure 9:
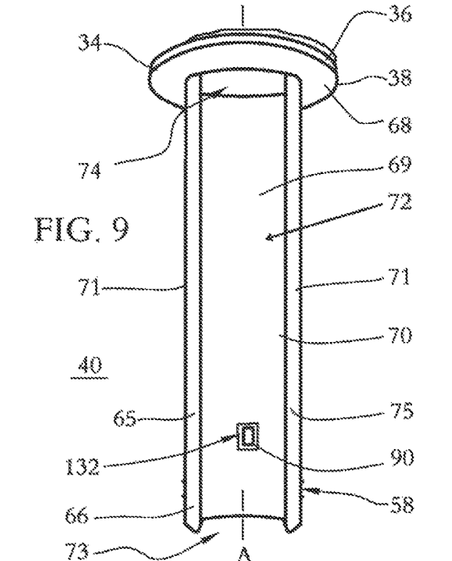
FIG. 9 is a perspective view of a component shown in FIG. 1.
Figure 10:
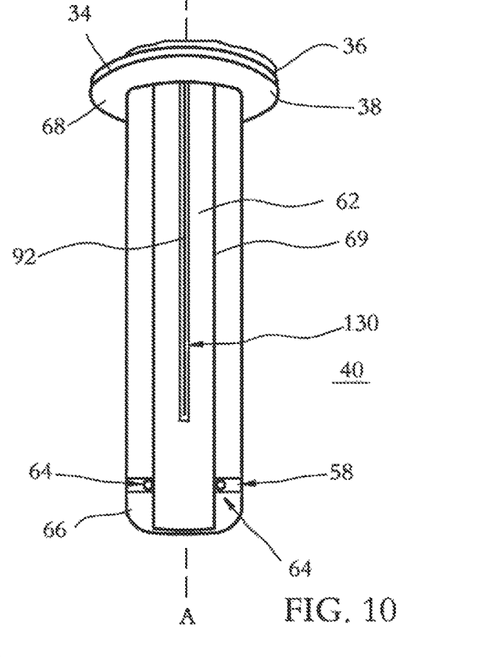
FIG. 10 is a perspective view of a component shown in FIG. 1.
Figure 11:
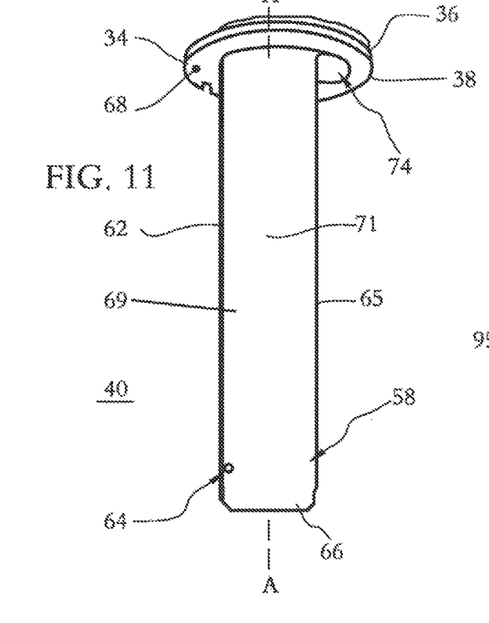
FIG. 11 is a side view of a component shown in FIG. 1.

In some embodiments, member 40 comprises a lumen 130 that extends into an outer surface of ridge 62 without extending through surface 70, as shown in FIG. 10, for example. Lumen 130 terminates in a cavity 132 that extends into surface 70 without extending through the outer surface of ridge 62, as shown in FIG. 9. Lumen 130 is in communication with an aperture 134 extending parallel to axis A through flange 68, as shown in FIG. 12. In some embodiments, lumen 130 does not extend through surface 70 or the outer surface of ridge 62 such that lumen 130 is embedded within a wall thickness of member 40, and is thus concealed from view. A light source, such as, for example, light source 90 is positioned in cavity 132 such that a wire, such as, for example, wire 92 connected to light source 90 extends through lumen 130 and aperture 134, as shown in FIGS. 9, 10 and 12. In some embodiments, wire 92 is used to provide power to light source 90. Light source 90 is configured to illuminate at least a portion of passageway 72.

Figure 16:
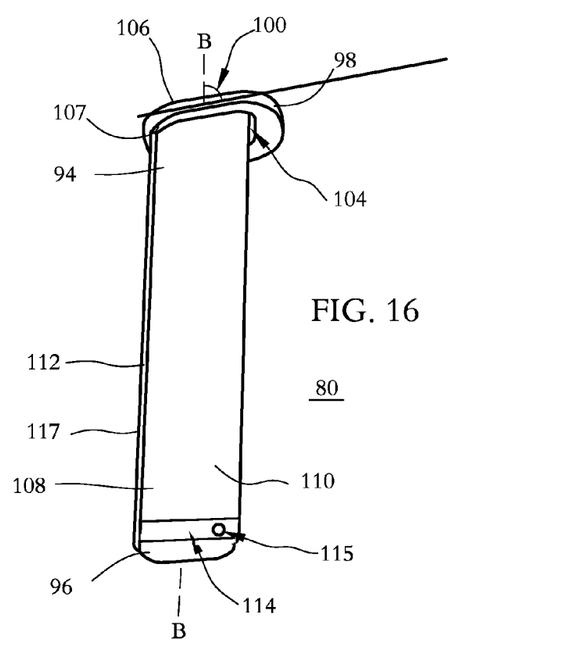
FIG. 16 is a perspective view of a component shown in FIG. 1.

Member 80 extends along a longitudinal axis B between an end 94 and an opposite end 96. End 94 comprises a lip 98 extending at an angle 100 relative to axis B, as shown in FIG. 16. An outer surface of lip has a cross sectional configuration perpendicular to axis B that defines a rounded square or circle. Lip 98 is configured for engagement with surface 56 to move member 24 between first and second configurations or orientations, as will be discussed. Lip 98 includes an inner surface 102 defining an opening 104 having a cross sectional configuration perpendicular to axis B that defines a rounded square or circle. Lip 98 includes planar upper and lower surfaces 106, 107 that extend parallel to one another. Surfaces 106, 107 extend at angle 100 relative to axis B. Member 80 includes a planar wall 108 that extends between opposite planar side walls 110. Wall 108 includes an outer surface 112 that is convexly curved between outer surfaces of walls 110 and configured to engage the concave portion of portion 105. Wall 108 includes an inner surface opposite surface 112 that is planar between inner surfaces of walls 110. In some embodiments, the inner surface of wall 108 is continuously planar between walls 110. The inner surface of member 80 includes interfaces between wall 108 and walls 110 that are each concavely curved. The interfaces between inner surfaces of wall 108 and walls 110 are configured to engage the concave interfaces between outer surfaces of portions 95 and portion 105. Surface 102, an inner surface of wall 108 and inner surfaces of walls 110 define a conduit 116. In some embodiments, member 80 is made entirely of molded plastic. In some embodiments, cannula 22 is made entirely radiopaque materials to aid in fluoroscopic visualization. In some embodiments, member 80 is radiopaque to aid in fluoroscopic visualization. In some embodiments, only a distal tip of member 80 is radiopaque to aid in fluoroscopic visualization.

In some embodiments, surface 102 is continuously curved between walls 110. In some embodiments, angle 100 is an acute angle. In some embodiments, angle 100 is angle between about 45 and about 90 degrees. In some embodiments, lip 98 may be disposed at alternate orientations, relative to axis B, such as, for example, transverse, perpendicular and/or other angular orientations such as acute or obtuse, co-axial and/or may be offset or staggered. In some embodiments, opening 104 may have various cross section configurations, such as, for example, oval, oblong, triangular, rectangular, square, polygonal, irregular, uniform, non-uniform, variable, tubular and/or tapered. In some embodiments, all or only a portion of surface 102, surface 106 and/or surface 112 may be variously configured and dimensioned, such as, for example, planar, concave, polygonal, irregular, uniform, non-uniform, staggered, tapered, consistent or variable.

Member 80 comprises a groove 114 adjacent end 96 extending into an outer surface of member 80 without extending through the inner surface of member 80. Groove 114 is configured for disposal of wire 60. In some embodiments, groove 114 extends perpendicular to axis B. In some embodiments, member 80 comprises a ridge 117 extending outwardly from the outer surface of member 80 that interrupts groove 114. In some embodiments, ridge 117 extends parallel to axis B. In some embodiments, ridge 117 bisects groove 114 into two equal length portions. That is, groove 114 comprises a first portion on one side of ridge 117 and a second portion on another side of ridge 117. In some embodiments, groove 114 comprises an opening 115 in each of side walls 110 that extend through inner and outer surfaces of member 80, as shown in FIGS. 7 and 8. In some embodiments, one opening 115 extends through one of side walls 110 and the other opening 115 extends through the other side wall 110. In some embodiments, openings 115 are aligned and/or coaxial. In some embodiments, side walls 110 extend parallel to one another and openings 115 each extend perpendicular to side walls 110. An end 61 of wire 60 is disposed in one of openings 115 and an opposite end 63 of wire 60 is disposed in the other opening 115, as shown in FIGS. 7 and 8. Ends 61, 63 are disposed in openings 115 such that ends 61, 63 and/or wire 60 are fixed relative to member 80. In some embodiments, ends 61, 63 are looped within openings 115. In some embodiments ends 61, 63 can be fixed to member 80 by means of ultrasonic welding, over-molding of plastic, adhesive, heat-staking, press-fit, twisting as well as mechanical means such as, for example, fasteners, screws, clips, rivets and the like. In some embodiments, all or only a portion of groove 114 may be variously configured and dimensioned, such as, for example, planar, concave, polygonal, irregular, uniform, non-uniform, staggered, tapered, consistent or variable. In some embodiments, groove 114 may be disposed at alternate orientations, relative to axis B, such as, for example, transverse, perpendicular and/or other angular orientations such as acute or obtuse, co-axial and/or may be offset or staggered. In some embodiments, openings 115 may be disposed at alternate orientations, relative to side walls 110, such as, for example, transverse, perpendicular and/or other angular orientations such as acute or obtuse, co-axial and/or may be offset or staggered. In some embodiments, openings 115 may have various cross section configurations, such as, for example, oval, oblong, triangular, rectangular, square, polygonal, irregular, uniform, non-uniform, variable, tubular and/or tapered.

Figure 15:
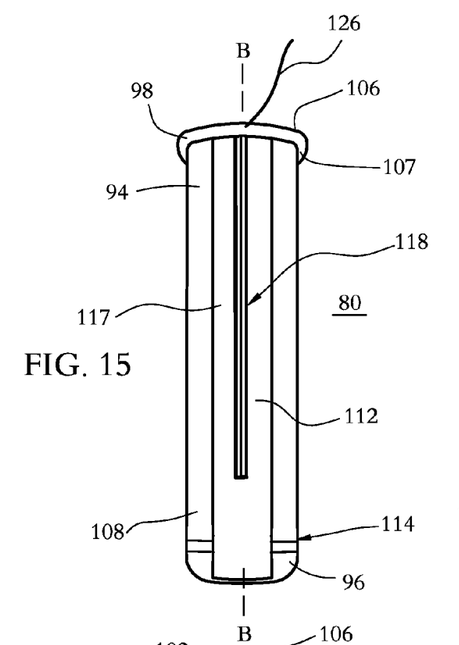
FIG. 15 is a perspective view of a component shown in FIG. 1.
Figure 17:
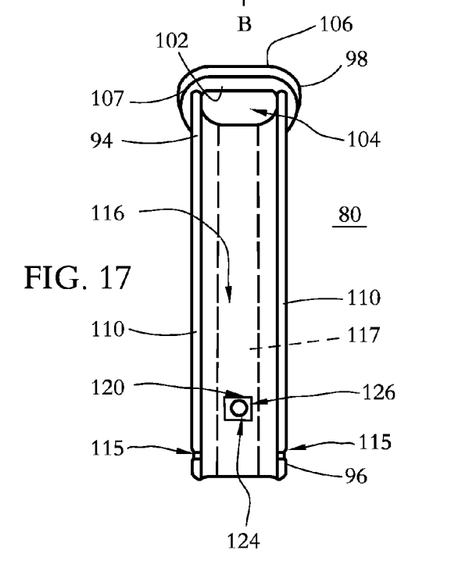
FIG. 17 is a side view of a component shown in FIG. 1.
Figure 18:
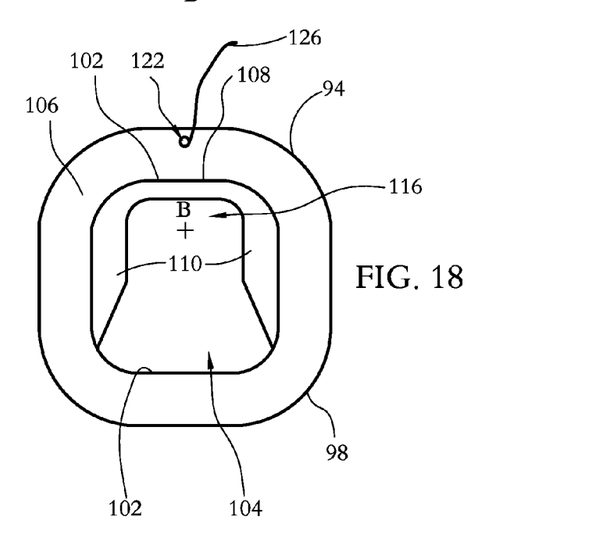
FIG. 18 is a top view of a component shown in FIG. 1.
Figure 19:
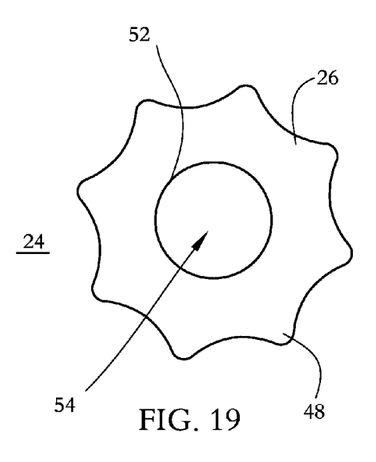
FIG. 19 is a top view of a component shown in FIG. 1.
Figure 20:
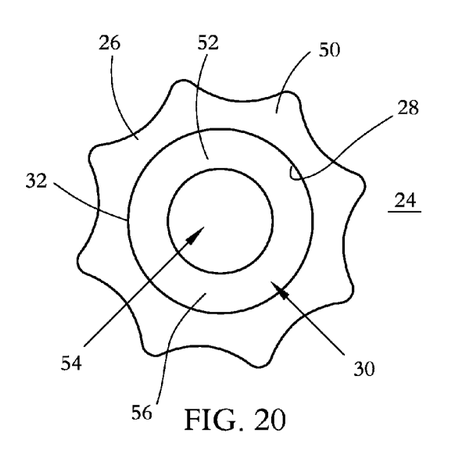
FIG. 20 is a bottom view of a component shown in FIG. 1.

In some embodiments, member 80 comprises a lumen 118 that extends into surface 112 without extending through the inner surface of wall 108. In some embodiments, lumen 118 extends through ridge 117. Lumen 118 terminates in a cavity 120 that extends into the inner surface of wall 108 without extending through surface 112, as shown in FIG. 17. Lumen 118 is in communication with an aperture 122 extending parallel to axis B through lip 98. In some embodiments, lumen 118 does not extend through the inner surface of wall 108 or surface 112 such that lumen 118 is embedded within a wall thickness of wall 108, and is thus concealed from view. A light source 124, such as, for example, a light emitting diode (LED) is positioned in cavity 120 such that a wire 126 connected to light source 124 extends through lumen 118 and aperture 122, as shown in FIGS. 15, 17 and 18. In some embodiments, wire 126 is used to provide power to light source 124. Light source 124 is configured to illuminate at least a portion of conduit 116. In some embodiments, light source 124 is embedded within member 80 such that light source 124 is permanently fixed to member 80. In some embodiments, light source 124 is embedded within member 80 and at least a portion of member 80 is transparent or translucent to allow light from light source 124 to pass through member 80. In some embodiments, cannula 22 includes a battery configured to power light source 124.

In assembly, operation and use, surgical system 20, similar to that described above, is employed, for example, with a minimally invasive surgical procedure for spinal and neurosurgical applications with a patient. For example, during spine surgery, a surgeon will make an incision in the skin of a patients back over vertebrae to be treated. One or more dilators may be employed to gradually separate the muscles and create a portal through which the surgery may be performed. Cannula 22 is positioned adjacent the surgical site over the small incision. Cannula 22 is passed through the incision.

When cannula 22 is passed through the incision, end 96 is movably positioned in passageway 72 such that surface 70 of member 40 engages outer surfaces of side walls 110 and ridge 62 is positioned opposite ridge 117, as shown in FIG. 7, for example. Wire 60 is positioned in grooves 58, 114 such that end 61 is disposed in one of openings 115 and end 63 is disposed in the other opening 115 to fix wire 60 relative to member 80, as discussed above and shown in FIGS. 7 and 9, for example. Wire 60 is positioned in groove 114 such that wire 60 extends through openings 64, as shown in FIGS. 7 and 8, for example. When wire 60 extends through openings 64, a bent portion 67 of wire 60 is positioned in passageway 72, as shown in FIGS. 7 and 8. Member 24 is positioned relative to member 40 with member 24 in a first configuration or orientation, shown in FIGS. 1, 1A, 3, 5 and 7, such that surface 56 is spaced apart from surface 106 and/or is positioned relative to lip 98 such that member 24 does not exert any force on lip 98 and member 80 extends parallel to axis A, as shown in FIG. 1A, for example. When member 80 extends parallel to axis A, member 24 is in the first configuration. When member 24 is in the first configuration, surface 56 is spaced apart from surface 106 and/or is positioned relative to lip 98 such that member 24 does not exert any force on lip 98.

When member 24 is in the first configuration, portions 77 of wire 60 are disposed in groove 114 and portions 79 of wire 60 is disposed in groove 58 such that wire 60 does not protrude above the outer surface of member 40 and/or no portion of wire 60 is proud relative to the outer surface of member 40, as shown in FIG. 7. That is, wire 60 is disposed in groove 58 such that an outer surface of wire 60 engages a surface of member 40 that defines groove 58 when member 24 is in the first configuration. In some embodiments, groove 114 has a depth that is greater than a maximum width or height of wire 60 such that portions 77 are disposed completely within groove 114 when the outer surface of wire 60 engages the surface that defines groove 114. In some embodiments, groove 58 has a depth that is greater than a maximum width or height of wire 60 such that portions 79 are disposed completely within groove 58 when the outer surface of wire 60 engages the surface that defines groove 58. In some embodiments, wire 60 is disposed in groove 58 such that an outer surface of wire 60 engages a surface of member 40 that defines groove 58 along the entire length of groove 58 when member 24 is in the first configuration. That is, wire 60 extends along entire lengths of each of the first and second portions of groove 58 that are bisected by ridge 62. When portions 77 of wire 60 are disposed in groove 114 and portions 79 of wire 60 is disposed in groove 58, wire 60 is in a first configuration or orientation, as shown in FIGS. 1, 3, 5 and 7. When wire 60 is in the first configuration, wire 60 is held closely to the outer surface of cannula 22 such that no portion of wire 60 protrudes outwardly from the exterior surface of cannula 22 in a manner that would engage tissue to fix cannula 22 relative to the anatomy of the patient.

Member 24 is rotated about axis A to move member 24 from the first configuration of member 24 to a second configuration of member 24 in which surface 56 engages surface 106 and member 80 extends at an acute angle relative to axis A, as shown in FIGS. 2, 2A, 4, 6 and 8. As member 24 is rotated about axis A, member 24 translates axially in the direction shown by arrow C. As member 24 moves in the direction shown by arrow C. surface 56 applies a force upon surface 106 such that surface 107 engages surface 128. The force applied to lip 98 causes lip 98 to be parallel to flange 68. Due to the configuration of lip 98 and flange 68, as lip 98 moves from the transverse relationship with flange 68 when member 24 is in the first configuration to the parallel relationship with flange 68 when member 24 is in the second configuration, member 80 deflects outwardly away from member 40 such that member 80 extends at an acute angle relative to axis A, as shown in FIGS. 2, 2A, 4, 6 and 8. When member 80 extends at an acute angle relative to axis A, member 24 is in the second configuration. In some embodiment, the acute angle is equal to angle 100. When member 24 in the second configuration, outer surfaces of members 40, 80 engage tissue, such as, for example, soft tissue, ligaments, tendons, cartilage and/or bone. Members 40, 80 space apart tissue and create access and/or a surgical pathway to a surgical site. That is, when member 24 in the second configuration, an item, such as, for example, a surgical instrument may be inserted through a pathway defined by passageway 72 and conduit 116 and/or a surgical procedure may be performed within the pathway.

As member 24 moves from the first configuration to the second configuration, portions 79 of wire 60 deflect outwardly from member 40 such that portions 79 are spaced apart from groove 58, as shown in FIG. 8. As portions 79 of wire 60 deflect outwardly from member 40, portions 79 become spaced apart from groove 58, as shown in FIG. 8. As portions 79 of wire 60 deflect outwardly from member 40, portions 77 move out of groove 114 and engage axial surfaces 65, 75 and axial surfaces 87, 89 of member 80, as also shown in FIG. 8. When portions 79 are spaced apart from groove 58 and portions 77 are spaced apart from groove 114 and engage axial surfaces 65, 75, 87, 89, wire 60 is in a second configuration or orientation, as shown in FIGS. 2, 4, 6 and 8. As such, moving member 24 between the first and second configurations of member 24 moves wire 60 between the first and second configurations of wire 60. In some embodiments, wire 60 includes a portion 81 between each of portions 77, 79. As wire 60 moves from the first configuration of wire 60 to the second configuration of wire 60, portions 81 define a barb having a sharp point that penetrates tissue, such as, for example, surrounding muscle, to fix cannula 22 relative to the patient. In some embodiments, portions 81 are spaced apart from member 40 when wire is in the first configuration and engage one of surfaces 65, 75 when wire 60 is in the first configuration. In some embodiments, portions 81 are blunt or rounded.

In some embodiments, at least one of light sources 90, 124 are in an on position as member 24 moves from the first configuration to the second configuration. In some embodiments, at least one of light sources 90, 124 are moved from an off position to an on position after member 24 is moved from the first configuration to the second configuration. When light sources 90, 124 are in an on position, light sources 90, 124 emit light into the pathway defined by passageway 72 and conduit 116 to aid in visualization to perform a surgical procedure, for example. In some embodiments, light sources 90, 124 are configured to emit light without creating shadows, making cannula 22 useful for imaging purposes, for example.

Upon completion of the surgical procedure, member 24 is moved from the second configuration to the first configuration and cannula 22 is removed from the surgical site. As member 24 moves from the second configuration to the first configuration, wire 60 moves inwardly relative to cannula 22 such that portions 79 are disposed in groove 58, portions 81 engage surfaces 65, 75 and portions 77 are disposed in groove 114. That is, moving member 24 from the second configuration of member 24 to the first configuration of member 24 causes wire 60 to move from the second configuration of wire 60 to the first configuration of wire 60. As wire 60 moves from the second configuration of wire 60 to the first configuration of wire 60, wire 60 disengages tissue, such as, for example, surrounding muscle, allowing cannula 22 to move relative to the patient's anatomy.

It is envisioned that the use of microsurgical and image guided technologies may be employed to access, view and repair spinal deterioration or damage, with the aid of cannula 22. It is contemplated that a surgical procedure may employ other instruments that can be mounted with cannula 22, such as, for example, nerve root retractors, tissue retractors, forceps, cutter, drills, scrapers, reamers, separators, rongeurs, taps, cauterization instruments, irrigation and/or aspiration instruments, illumination instruments and/or inserter instruments.

Cannula 22 may be employed for performing spinal surgeries, such as, for example, laminectomy, discectomy, fusion, laminotomy, nerve root retraction, foramenotomy, facetectomy, decompression, spinal nucleus or disc replacement and procedures using bone graft and implantable prosthetics including plates, rods, and bone engaging fasteners.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A surgical instrument, comprising:
    a first member comprising an end surface and a body including an inner surface defining a throughhole;
    a second member extending along a first longitudinal axis between a first end comprising a flange and an opposite second end comprising a first groove having a holding member movably disposed therein, the second member comprising an inner surface defining a passageway; and
    a third member extending along a second longitudinal axis between a first end comprising a lip and an opposite second end that is movably positioned in the passageway, the lip extending at an acute angle relative to the second longitudinal axis, the second end of the third member comprising a second groove having the holding member movably disposed therein,
    wherein the holding member is movable between a first configuration in which the holding member is disposed in the second groove and first and second portions of the holding member are positioned in the first groove and a second configuration in which the holding member is spaced apart from the second groove and the first and second portions of the holding member are spaced apart from the first groove.

2. A surgical instrument as recited in claim 1, wherein the first and second portions of the holding member engage an outer surface of the second member when the holding member is in the first configuration and are spaced apart from the outer surface when the holding member is in the second configuration.

3. A surgical instrument as recited in claim 1, wherein the holding member is fixed to the third member.

4. A surgical instrument as recited in claim 1, wherein the holding member is wire.

5. A surgical instrument as recited in claim 1, wherein the holding member is wire comprising nitinol.

6. A surgical instrument as recited in claim 1, wherein the holding member is wire comprising spring steel.

7. A surgical instrument as recited in claim 1, wherein the first and second portions of the holding member each define a barb that is spaced apart from the instrument and configured to penetrate tissue when the holding member is in the second configuration.

8. A surgical instrument as recited in claim 1, wherein:
    the second member comprises first and second side walls each extending from an end wall;

the first portion of the holding member extends outwardly from the first side wall when the holding member is in the second configuration; and the second portion of the holding member extends outwardly from the second side wall when the holding member is in the second configuration.

9. A surgical instrument as recited in claim 1, wherein the first member is movable between a first orientation in which the end surface is spaced apart from the lip and the third member extends parallel to the first longitudinal axis and a second orientation in which the end surface engages the lip and the third member extends at an acute angle relative to the first longitudinal axis.

10. A surgical instrument as recited in claim 9, wherein the first member moves between the first and second orientations by rotating the first member relative to the second member.

11. A surgical instrument as recited in claim 9, wherein the inner surface of the first member comprises an internal thread form and an outer surface of the first end of the second member comprises an external thread form that engages the internal thread form to move the first member between the first and second orientations.

12. A surgical instrument as recited in claim 1, wherein the body comprises a projection extending inwardly from the inner surface of the body, a bottom surface of the projection defining the end surface.

13. A surgical instrument as recited in claim 1, wherein at least one of the second member and the third member include a light source configured to illuminate the passageway.

14. A surgical method comprising:
providing the surgical instrument of claim 1;
creating an incision;
creating a surgical pathway from the incision to a surgical site;
positioning the surgical instrument in the pathway with the first member in the first configuration; and
moving the first member from a first orientation in which the end surface is spaced apart from the lip and the third member extends parallel to the first longitudinal axis to a second orientation in which the end surface engages the lip and the third member extends at an acute angle relative to the first longitudinal axis to create a working channel.

15. A surgical method as recited in claim 14, wherein moving the first member from the first orientation to the second orientation comprises rotating the first member relative to the second member.

16. A surgical method as recited in claim 14, wherein:
the inner surface of the first member comprises an internal thread form and an outer surface of the first end of the second member comprises an external thread: and
moving the first member from the first orientation to the second orientation comprises engaging the external thread form with the internal thread form.

17. A surgical method as recited in claim 14 wherein moving the first member from the first orientation to the second orientation moves the holding member between the first configuration and the second configuration.

18. A surgical method as recited in claim 17, wherein the first and second portions of the holding member penetrate tissue when the holding member is in the second configuration.

19. A surgical method as recited in claim 14, wherein:
at least one of the second member and the third member include a light source; and
the method further comprises moving the light source from an off position to an on position to illuminate the passageway.

20. A surgical instrument, comprising:
a first member comprising a body including an inner surface defining a throughhole, the inner surface comprising an internal thread form, the first member further comprising a projection extending inwardly from the inner surface of the body, a bottom surface of the projection defining an end surface of the first member;
a second member extending along a first longitudinal axis between a first end comprising a flange and an opposite second end comprising a first groove having a holding member movably disposed therein, the holding member comprising a shape memory material, the second member comprising an inner surface defining a passageway, the first end of the second member comprising an outer surface having an external thread form that engages the internal thread form; and
a third member extending along a second longitudinal axis between a first end comprising a lip and an opposite second end that is movably positioned in the passageway, the lip extending at an acute angle relative to the second longitudinal axis, the second end of the third member comprising a second groove having the holding member movably disposed therein, the holding member being fixed relative to the third member,
wherein the first member is movable between a first orientation in which the end surface is spaced apart from the lip and the third member extends parallel to the first longitudinal axis and a second orientation in which the end surface engages the lip and the third member extends at an acute angle relative to the first longitudinal axis,
wherein the first member moves between the first and second orientations by rotating the first member relative to the second member,
wherein moving the first member between the first and second orientations moves the holding member between a first configuration in which the holding member is disposed in the second groove and first and second portions of the holding member are positioned in the first groove and a second configuration in which the holding member is spaced apart from the second groove and the first and second portions of the holding member are spaced apart from the first groove,
wherein the first and second portions of the holding member each define a barb that is spaced apart from the instrument and configured to penetrate tissue when the holding member is in the second configuration,
wherein at least one of the second member and the third member include a light source configured to illuminate the passageway.

* * * * *